United States Patent [19]

Fehr et al.

[11] Patent Number: 5,521,151
[45] Date of Patent: May 28, 1996

[54] TETRALINIC NITRILES, THEIR USE AS PERFUMING INGREDIENTS AND ALDEHYDE INTERMEDIATES FOR THEIR PREPARATION

[75] Inventors: Charles Fehr, Versoix; François Delay, Carouge; Pierre-Alain Blanc, Crassier; Nathalie Chaptal-Gradoz, Geneva, all of Switzerland

[73] Assignee: Firmenich S.A., Geneva, Switzerland

[21] Appl. No.: 366,949

[22] Filed: Dec. 29, 1994

[30] Foreign Application Priority Data

Jan. 25, 1994 [CH] Switzerland ................. 209/94
Dec. 8, 1994 [CH] Switzerland ................ 3714/94

[51] Int. Cl.⁶ ..................................... A61K 7/46
[52] U.S. Cl. ..................... 512/6; 558/411; 512/17; 568/440; 252/174.11; 252/8.6; 424/76.4
[58] Field of Search ............. 512/6, 17; 568/440; 558/411; 252/174.11, 86; 424/76.4

[56] References Cited

U.S. PATENT DOCUMENTS

| | | | |
|---|---|---|---|
| 5,087,770 | 2/1992 | Aucun | 568/327 |
| 5,162,588 | 11/1992 | Fehr et al. | 568/328 |
| 5,204,322 | 4/1993 | Frank | 512/6 |
| 5,300,488 | 4/1994 | Narula et al. | 512/6 |
| 5,324,875 | 6/1994 | Fehr et al. | |
| 5,346,884 | 9/1994 | Narula et al. | 512/6 |

FOREIGN PATENT DOCUMENTS

| | | | |
|---|---|---|---|
| 405427 | 1/1991 | European Pat. Off. | 512/6 |
| 9313054 | 7/1993 | WIPO | 512/6 |

OTHER PUBLICATIONS

*J. Chem. Soc.*, 1965, Notes: 297. "A convenient One-step Conversion of Aldehydes Into Nitriles", by T van Es.

J. March, Advanced Organic Chemistry: Reactions, Mechanisms and Structure, 3rd Edition, section 7–40, John Wiley & Sons, USA 1985.

*Perfumer & Flavorist*, vol. 4, Dec./Jan. 1980, "Nitriles in perfumery" by Dr. Robert DeSimone.

Primary Examiner—James H. Reamer
Attorney, Agent, or Firm—Pennie & Edmonds

[57] ABSTRACT

We disclose a novel nitrile, i.e. 5,6,7,8-tetrahydro-3,5,5,6,7,8,8-heptamethyl-2-naphthalenecarbonitrile, a perfuming ingredient having a musky, earthy odor, and which is remarkably stable in particularly aggressive media such as for instance antiperspirant bases. This compound may present itself as a racemate or in the form of one of its optically active isomers.

Said isomers can be obtained from aldehydes, namely (−)-(6S,7S) and (+)-(6R,7R)-5,6,7,8-tetrahydro-3,5,5,6,7,8,8-heptamethyl-2-naphtalenecarbaldehyde, which aldehydes are not only useful as starting products for the preparation of the corresponding nitriles, but also as perfuming ingredients.

10 Claims, No Drawings

TETRALINIC NITRILES, THEIR USE AS PERFUMING INGREDIENTS AND ALDEHYDE INTERMEDIATES FOR THEIR PREPARATION

BRIEF SUMMARY OF THE INVENTION

The invention provides novel 5,6,7,8-tetrahydro-3,5,5,6,7,8,8-heptamethyl-2-naphthalenecarbonitrile, as a racemate or in the form of one of its optically active isomers.

It further relates to its (−)-(6S,7S) and (+)-(6R,7R) enantiomers.

It is another object of the invention to provide a method to confer, enhance, improve or modify the odor properties of a perfuming composition or a perfumed article, which method comprises adding to said composition or article a fragance effective amount of one of the above-mentioned nitriles.

Another object of the invention is to provide perfuming compositions or perfumed articles resulting from the above-mentioned method.

In addition, the invention also relates to processes for the preparation of the compounds cited above, wherein there are used as starting products the corresponding aldehydic analogues. The use of some of the latter aldehydes as perfuming ingredients is also an object of the invention.

BACKGROUND OF THE INVENTION

The present invention relates to the field of perfumery and, more particularly, to a novel compound, i.e. 5,6,7,8-tetrahydro-3,5,5,6,7,8,8-heptamethyl- 2-naphthalenecarbonitrile, in the form of a racemic compound or of one of its optically active isomers such as for example (−)-(6S,7S)-5,6,7,8-tetrahydro- 3,5,5,6,7,8,8-heptamethyl-2-naphthalenecarbonitrile and (+)-(6R,7R)-5,6,7,8-tetrahydro-3,5,5,6,7,8,8-heptamethyl-2-naphthalenecarbonitrile.

It is a further object of the invention to provide the novel aldehydic tetralin derivatives used as intermediates for the preparation of said isomers.

The above-mentioned nitrile is a nitrogen-containing analogue of 5,6,7,8-tetrahydro-3,5,5,6,7,8,8-heptamethyl-2-naphthalenecarbaldehyde, a much appreciated perfuming ingredient with a musky character, described in U.S. Pat. No. 5,162,588. We have now discovered that the use in perfumery of the compounds of the instant invention can be highly advantageous when compared to that of said prior art carbaldehyde, namely upon employing these compounds in highly aggressive media such as for example those of consumer articles of the soap, deodorant or detergent type.

DETAILED DESCRIPTION OF THE INVENTION

It has in fact been observed that 5,6,7,8-tetrahydro-3,5,5,6,7,8,8-heptamethyl- 2-naphthalenecarbonitrile possesses an earthy and musky odor, the bottom note of which is provided with a humus-like and earthy character which strongly resembles the odor of its aldehydic analogue above-cited. Although the note of the racemic compound is similar to that developed by its enantiomers (−)-(6S,7S) and (+)-(6R,7R), the odor character of the latter is distinct from that of the racemate insofar as (−)-(6S,7S)-5,6,7,8-tetrahydro-3,5,5,6,7,8,8-heptamethyl-2-naphthalenecarbonitrile possesses a stronger and woodier note than its (+)-(6R,7R) enantiomer. Thus, in what concerns the quality of the odor note, the compounds of the invention turn out to be just as precious and useful as the known carbaldehyde and can replace the latter in its typical applications (see for example U.S. Pat. No. 5,162,588). This is an unexpected and very advantageous result insofar as, as is apparent from the examples presented further on, the nitriles of the invention are chemically stable in the media where their aldehydic analogues may present stability problems. If, in addition, one takes into account the fact that these nitriles revealed themselves even more tenaceous on textiles than the corresponding aldehydes, one understands immediately how valuable the compounds of the invention are, in particular for perfuming detergents and fabric softeners.

It should be pointed out that the resemblance and comparable olfactive value between the aldehydes and the nitriles observed in the present case is a surprising result in view of the prior art. Indeed, upon a comparative study between analogues having carboxyl or nitrile functional groups, reported by R. De Simone in Perfumer and Flavorist 4, 1 (1980), it had been established that, for compounds with tetralinic or indanic structures, the nitrile analogues of strongly musky carboxylic compounds could present far weaker odors, or even be practically odorless. In particular, the nitrile of Tonalid® (origin:Polak's Frutal Works, USA), the strongest keto-musk known at the time, had been shown to possess an odor far weaker than that of the nitriles of other commercial ketonic compounds, which were known to be less interesting and useful than Tonalid®. It therefore results from this study that the olfactive value of the nitrile is totally unpredictable, even when it is known that the carboxylic analogue thereof possesses interesting and useful properties.

The results of the above-mentioned study were later confirmed by the applicant, holder of the present application. It was in fact observed, as a result of an exhaustive study of Tonalid® and Celestolide® (origin:IFF Inc. USA) derivatives such as epoxides, alcohols, esters, aldehydes, methyl ketones and nitriles, and upon evaluation of these derivatives by a panel of expert perfumers, that the nitriles were inferior, from an olfactive point of view, to the corresponding aldehydes, epoxides and ketones, both with regard to the quality and the intensity of the odor, and this for the two series of compounds. In particular, the perfumers found that the nitrile of Tonalid®, having the structure

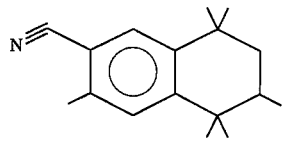

possessed a weak musky odor, accompanied by a nitrile and pharmaceutical note.

It is thus surprising to observe that, in spite of the fact that the compounds of the present invention and their analogues described in U.S. Pat. No. 5,162,588 only have one methyl group more than Tonalid® and its corresponding anlogues, their olfactive behaviour is entirely distinct from that of the known compounds, even as regards the quality and the relative strength of the odor within the two families of compounds.

The present invention thus provides novel nitriles possessing surprising odor properties relative to those of the known compounds of closest structure and comparable to those of the known aldehyde analogue and which, furthermore, have a perfectly stable behaviour in difficult media such as soaps, detergents and deodorants. Consequently, these nitriles can be of an alternative use to that of said aldehyde, which use will be all the more advantageous in the mentioned difficult media.

As a result of its structure, 5,6,7,8-tetrahydro-3,5,5,6,7,8,8-heptamethyl- 2-naphthalenecarbonitrile can present itself in two isomeric forms of cis and trans configuration, of which the trans configuration isomer is preferred according to the invention. Nevertheless, the mixtures of cis and trans isomers are also excellent perfuming ingredients, providing comparable fragrance effects.

These two racemic isomers can themselves assume two distinct enantiomeric forms. As indicated above, the invention particularly concerns the two enantiomers of formula

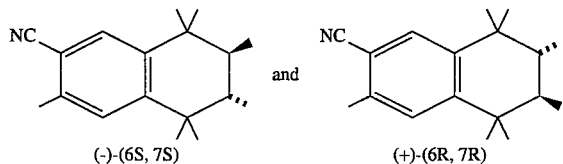

(−)-(6S, 7S)      and      (+)-(6R, 7R)

As previously cited, 5,6,7,8-tetrahydro-3,5,5,6,7,8,8-heptamethyl-2-naphthalenecarbonitrile, whether in racemic form or in the form of one of said enantiomers, can be used in analogous conditions to those of the use of 5,6,7,8-tetrahydro-3,5,5,6,7,8,8-heptamethyl-2-naphthalenecarbaldehyde, both as regards the nature of the compositions into which it can be incorporated, and the proportions in which it can be used. Such conditions are described in detail in U.S. Pat. No. 5,162,588 and, to this end, the examples of applications in perfumery there reported are hereby included by reference. Other applications of 5,6,7,8-tetrahydro-3,5,5,6,7,8,8-heptamethyl-2-naphthalenecarbonitrile, which particularly illustrate its chemical stability and remarkable tenacity, are presented further on.

It goes without saying that, although the alternative use of the nitriles is more advantageous for perfuming soaps, detergents and household products, fabric softeners, deodorants and antiperspirants, these compounds can also be used for perfuming other consumer articles, such as perfumes and colognes, shampoos and other hair-cair products, bath or shower gels and cosmetic preparations.

The compounds of the invention can be prepared by several methods. According to the invention, they are preferably prepared by reacting the oxime of 5,6,7,8-tetrahydro-3,5,5,6,7,8,8-heptamethyl-2-naphthalenecarbaldehyde with a dehydrating agent, namely acetic anhydride. The particular reaction conditions are described further on. Other dehydrating agents can of course be used. Detailed description of such agents is hereby superfluous, this type of reactions being well-known to the skilled person [see, for example, J. March, Advanced Organic Chemistry:Reactions, Mechanisms and Structure, 3rd ed., section 7–40, John Wiley & Sons, USA (1985)].

The starting oximes in this process are novel compounds which are also the object of the present invention. They can be prepared from the corresponding carbaldehyde by means of conventional methods and under the conditions described further on (see also J. Chem. Soc. 1965, 1564).

When it is desired to obtain the trans and cis configuration isomers of the nitrile of the invention, there will be used as starting products the corresponding isomers of the above-mentioned carbaldehyde and of the subsequent oxime. The preparation of 5,6,7,8-tetrahydro- 3,5,5,6,7,8,8-heptamethyl-2-naphthalenecarbaldehyde, as well as that of its cis and trans configuration isomers, is described in detail in U.S. Pat. No. 5,162,588.

The preparation of the corresponding enantiomeric aldehydes (−)-(6S,7S) and (+)-6R,7R) was carried out by a particular process which can be illustrated as follows:

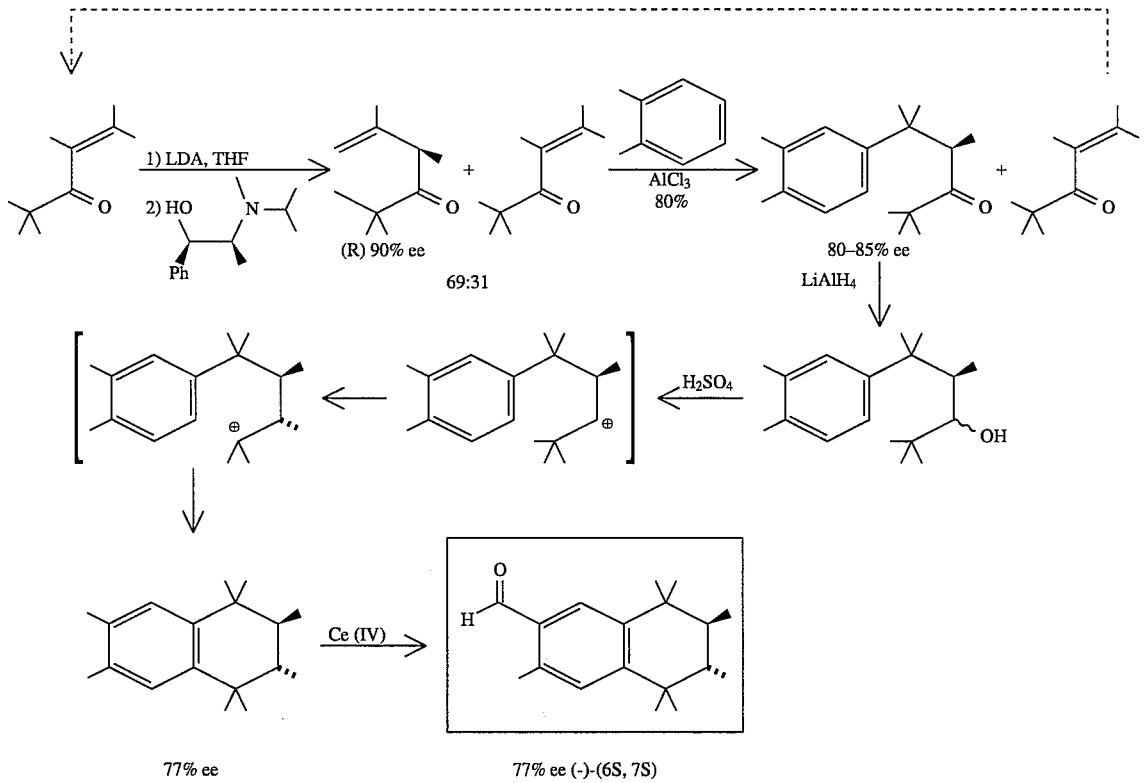

The (+)-(6R,7R) enantiomer can be obtained in a perfectly analogous manner, by replacing (−)-N-isopropylephedrine with (+)-N-isopropylephedrine. The (+)-(6R,7R) configuration aldehyde presented an optical purity equal to 82% ee.

The above-cited aldehydic compounds are not only useful as intermediates for the preparation of the nitrile derivatives of the invention, but also as perfuming ingredients. In particular, it has been found that (−)-( 6S ,7S )-5,6,7,8-tetrahydro-3,5,5,6,7,8,8-heptamethyl-2-naphthalenecarbaldehyde is the compound which possesses the best developed odor properties. Its musky, markedly earthy, slightly amber character is particularly powerful. It possesses a note which distinguishes itself from that of the (+)-(6R,7R) isomer insofar as the latter develops a fragrance of a less earthy character, with a woody side and the strength of which is clearly inferior. Their olfactive difference will be shown hereinafter by way of comparative application examples.

Thus, the present invention has also as its object said aldehydic compounds, as well as their use as perfuming ingredients for the preparation of perfumes or perfuming bases, or for perfuming a variety of consumer products.

The present invention will now be described in further detail by way of the following examples. In the examples of preparation of the compounds of the invention, the temperatures are indicated in degrees centigrade and the abbreviations have the usual meaning in the art.

EXAMPLE 1

Preparation of trans-5,6,7,8-tetrahydro-3,5,5,6,7,8,8-heptamethyl-2-naphthalenecarbonitrile a) Oxime of trans-5,6,7,8-tetrahydro-3,5,5,6,7,8,8-heptamethyl-2-naphthalenecarbaldehyde A flask under stirring was charged with 17.2 g (247.5 mmole) of hydroxylamine hydrochloride in 110 g of water. To this solution there were added 50 g (193.8 mmole) of trans-5,6,7,8-tetrahydro-3,5,5,6,7,8,8-heptamethyl- 2-naphthalenecarbaldehyde, 158 g of methanol and 290 g of diisopropylether. Finally, a solution of potassium carbonate (16.8 g, 121.7 mmole) in 90 g of water was introduced dropwise, without letting the temperature of the reaction mixture increase above 35°. After about 2 h of reaction, extraction with ether and concentration of the organic phase provided 60 g of raw product. The latter was crystallized in cyclohexane to provide 33 g of oxime of trans-5,6,7,8-tetrahydro- 3,5,5,6,7,8,8-heptamethyl-2-naphthalenecarbaldehyde, 91% pure (yield 72.9%). IR: 3256, 2970, 1610, 1502, 1464, 1393, 1362, 1312, 1222, 1112, 976, 940, 898, 856 cm$^{-1}$ NMR($^1$H, 360MHz): 0.97(d, J=6.5, 6H); 1.10(s, 6H); 1.32(s, 3H); 1.34(s, 3H); 1.59(m, 2H); 2.39(s, 3H); 7.17(s, 1H); 7.65(s, 1H); 7.93(broad s, 1H exchange with D$_2$O); 8.36(s, 1H) δppm NMR($^{13}$C, 360MHz): 13.8(2q); 19.6(q); 25.4(q); 25.6(q); 29.4(q); 29.5(q); 37.7(s); 37.9(s); 39.2(d); 39.3(d); 125.9(d); 127.7(s); 129.6(d); 135.5(s); 143.9(s); 147.9(s); 149.6(d) δppm MS:273(20, M$^+$), 258(41), 240(13), 216(37), 202(100), 197(56), 184(88), 170(13), 156(16), 142(14), 128(12), 115(15), 91(11), 77 (8), 69(5), 57(75), 43(37).

b) 76 G (0.745 mole) of acetic anhydride were heated to 120°, during 1 h, then, during 4½ h, there was added a solution of the raw oxime prepared according to a) (136.5 g; ~0.5 mole) in 1500 ml (1573 g) of acetic acid. After concentrating the reaction mixture, there were obtained 281 g of a partially solidified raw product having a dark color. This was taken into 400 g of cyclohexane and the precipitate was filtered. In order to completely eliminate the acetic acid, the solid was retaken in CHCl$_3$ and washed with NaHCO$_3$. After concentrating the product thus treated, there were obtained 64.5 g of a product 92.1% pure. The latter was further purified by crystallizing in cyclohexane to provide trans-5,6,7,8-tetrahydro- 3,5,5,6,7,8,8-heptamethyl-2-naphthalenecarbonitrile 98.5% pure. IR: 2969, 2873.5, 2223, 1610, 1500, 1474.5, 1392, 1364, 1220, 1112, 1025, 926, 866 cm$^{-1}$ NMR($^1$H, 360MHz): 0.97(d, J=6.5, 6H); 1.05(s, 3H); 1.07(s, 3H); 1.28(s, 3H); 1.29(s, 3H); 1.56(m, 2H); 2.47(s, 3H); 7.25(s, 1H); 7.59(s, 1H) δppm NMR($^{13}$C, 360MHz): 13.7(q); 13.8(q); 20.0(q); 25.3(q); 25.6(q); 29.2(q); 29.4(q); 37.7(s); 38.3(s); 39.0(2d); 110.1(s); 118.8(s); 129.0(d); 132.0(d); 137.7(s); 144.3(s); 151.2(s) δppm MS: 255(9, M$^+$), 240(22), 198(55), 184(100), 168(6), 156(10), 140(5), 127(5), 115(6), 57(38), 43(21).

Although there is described here-above the preparation of the trans isomer, the same method can be applied for the preparation of the other isomer, or yet of a mixture of the two.

EXAMPLE 2

Preparation of (−)-(6S,7S)- and of (+)-(6R,7R)-5,6,7,8-tetrahydro-3,5,5,6,7,8,8-heptamethyl- 2-naphthalenecarbonitrile a) 2,2,4,5-Tetramethyl-4-hexen-3-one 30.8 g (0.2 mole) of 2,2,4,5-tetramethyl-5-hexen-3-one were heated to 100° in 100 ml of toluene in the presence of 3.08 g of p-toluenesulfonic acid. After 24 h, the mixture was cooled down and extracted with ether. After neutralizing with an aqueous solution saturated with NaHCO$_3$, the organic phase was washed with water, then with a solution saturated with NaCl, and dried with Na$_2$SO$_4$. Evaporation and distillation of the residue, followed by fractional distillation, provided a fraction having B.p. 60°/1.06×10$^3$ Pa NMR($^1$H, 360MHz): 1.18(s, 9H); 1.57(s, 3H); 1.66(s, 3H); 1.77(s, 3H) δppm MS:m/z:154(3, M$^+$), 97(100), 69(62), 41(65), 39(20).

b) (−)-(R)-2,2,4,5-Tetramethyl-5-hexen-3-one

A solution of 15.4 g (100 mmole) of the ketone obtained as described under letter a) in 80 ml of tetrahydrofuran (THF) was added in 30 min at −45° to 200 mmole of lithiumdiisopropylamide in 150 ml de THF. A solution of 53.8 g (260 mmole) of (−)-N-isopropylephedrine in 250 ml of THF was added to the mixture in 1 h at −45°, then the whole was taken to −10° within 20 min. The mixture was then poured under vigorous stirring into a 20% HCl aqueous solution and extracted three times with ether. The organic phase was washed successively with bicarbonate, water and brine, then dried over Na$_2$SO$_4$ and concentrated under reduced pressure. The residue (17.6 g) was used without further purification. A sample of the obtained residue was purified by column chromatography (SiO$_2$), eluting with pentane:ether (19:1), to provide a product having 90% ee [α]$^{20}$D=−235° (c=2.2; CHCl$_3$).

The analytical data were identical to those described for a racemic sample Helv. Chim. Acta 1989, 72, 1537].

Replacing (−)-N-isopropylephedrine by (+)-N-isopropylephedrine and proceeding as indicated here-above, there was obtained (+)-(S)-2,2,4,5-tetramethyl- 5-hexen-3-one with 90% ee.

c) (−)-(R)-5-(3,4-Dimethyl-phenyl)-2,2,4,5-tetramethylhexan-3-one

Operating as indicated in Helv. Chim. Acta 1989, 72, 1537, there was treated at 0° the product obtained under letter b) with aluminium trichloride (1.2 eq. for 1 eq. of ketonic compound) in o-xylene. After extraction and evaporation of the solvent, there was obtained an oil (20.8 g) which, by fractional distillation, provided 15.3 g (yield 61%) of the desired ketone. $[\alpha]^{20}D=-102°$ (c=2.0; CHCl$_3$).

The spectroscopic characters were identical to those described for the racemic compound [Helv. Chim. Acta, op. cit.].

In an analogous manner, there was obtained the corresponding (+)-(S) isomer $[\alpha]^{20}D=+109°$ (c=2.2; CHCl$_3$).

d) (−)-(2S,3S)-1,2,3,4-Tetrahydro-1,1,2,3,4,4,6,7-octamethylnaphthalene

The compounds described under letter c) were reduced using lithium aluminiumhydride in ether, as indicated in Helv. Chim. Acta, op. cit. The product obtained was cyclised either by treatment with methanesulfonic acid and P$_2$O$_5$, or with sulfuric acid (15 g) in 20 ml of CH$_2$Cl$_2$ at −10° for 15min. Extraction with ether, followed by crystallisation in ethyl alcohol, provided 4.92 g of the desired compound and an oil having a content of 2.8 g in the same compound. $[\alpha]^{20}D=-37°$ (c=0.8; CHCl$_3$).

The corresponding (+) isomer was obtained in an analogous manner. $[\alpha]^{20}D=+40°$ (c=1.0; CHCl$_3$).

The spectroscopic characters were identical to those described for the racemic compound [Helv. Chim. Acta, op. cit.].

e) (−)-(6S,7S)-5,6,7,8-Tetrahydro-3,5,5,6,7,8,8-heptamethyl-2-naphthalenecarbaldehyde Operating as indicated in Helv. Chim. Acta, op. cit., the compound obtained under letter d) was oxidized by means of Ce(NH$_4$)$_2$(NO$_3$)$_6$. To this end, the reaction took place in methanol at 50°. The product obtained was purified by column chromatography (SiO$_2$), eluting with pentane:ether (97:3), to provide 2.0 g of naphthalenecarbaldehyde in 61% yield. A sample was recrystallized in ethyl alcohol. $[\alpha]^{20}D=-39°$ (c=0.85; CHCl$_3$); about 77% ee Operating in a similar manner, there was obtained the corresponding (+) compound $[\alpha]^{20}D=+42°$ (c=1.08; CHCl$_3$); about 82% ee.

The spectroscopic characters were entirely identical to those described for the corresponding racemic compound [Helv. Chim. Acta, op. cit.].

f) (−)-(6S,7S)-5,6,7,8-Tetrahydro-3,.5,5,6,7,8,8-heptamethyl-2-naphthalenecarbonitrile and its corresponding (+)-(6R,7R)- isomer Proceeding in an analogous manner as that described by T. van Es [J. Chem. Soc., 1965, 1564] and using as starting products the two enantiomers of the naphthalenecarbaldehyde obtained under letter e), the corresponding carbonitriles were obtained. Thus, 0.800 g (3.10mmole) of (−)-(6S,7S)-5,6,7,8-tetrahydro-3,5,5,6,7,8,8-heptamethyl-2-naphthalenecarbaldehyde were mixed with 0.280 g (4 mmole) of hydroxilamine hydrochloride, 0.420 g of sodium formate (6.20 mmole) and 5 ml of formic acid and the whole was heated to reflux during 45 min.

After cooling to 30°, the mixture was hydrolised with water and extracted three times with ether. After the usual treatments to separate the organic phase, washing with NaHCO$_3$ and NaCl, followed by drying over Na$_2$SO$_4$, the ether solution was treated with active carbon (0.200 g). The solution was thus heated to reflux during ¼ h, then concentrated. The obtained residue was purified by elution with cyclohexane:ethyl acetate (98:2) on a SiO$_2$ column (F 60; 40–60μ; 40 g). Evaporation of the solvent provided 0.620 g of a yellow solid which, upon recrystallisation (2 times with a mixture 1:1 of ether and cyclohexane), provided 0.360 g of (−)-(6S,7S)-5,6,7,8-tetrahydro- 3,5,5,6,7,8,8-heptamethyl-2-naphthalenecarbonitrile having $[\alpha]^{20}D=-39°$ (c=1.1; CHCl$_3$); about 77% ee.

Operating in an analogous manner, but using as starting product (+)-( 6R,7R)-5,6,7,8-tetrahydro-3,5,5,6,7,8,8-heptamethyl-2-naphthalenecarbaldehyde, the corresponding nitrile was obtained, having $[\alpha]^{20}D=+45°$ (c=0.94; CHCl$_3$); about 82% ee.

EXAMPLE 3

Stability test in an antiperspirant composition for roll-on

An antiperspirant composition, intended for application by means of a roll-on type device, was prepared by admixing the following ingredients:

|  | Ingredients | % by weight |
|---|---|---|
| A. | Natrosol 250 H[1] | 0.70 |
|  | Distilled water | 39.80 |
| B. | Locron L[2] | 20.00 |
|  | 1,3-Butylene-glycol | 2.00 |
|  | 95° Ethanol | 35.00 |
| C. | Perfume[3] | 1.00 |
|  | Chremophor RH 40[4] | 1.50 |
|  | Total | 100.00 |

[1] hydroxyethylcellulose, Hercules Co.
[2] aluminium hydroxychloride, Hoechst AG
[3] trans-5,6,7,8-tetrahydro-3,5,5,6,7,8,8-heptamethyl-2-naphthalene-carbonitrile, 10% solution in isopropyl myristate (MIP)
[4] hydrogenated and ethoxylated castor oil, BASF AG Natrosol was dispersed in water under vigorous stirring until obtaining a transparent gel. The ingredients of part B were then admixed amongst themselves and this mixture was poured into part A. Part C was then added and the transparent mixture thus obtained was then ready to be poured into roll-on type devices. This mixture, which developed the musky, earthy odor characteristic of the compound of the invention, was tested for 1 month, at 22° C. and at 40° C., for the stability of the odor developed. At the end of the testing period, a panel of expert perfumers judged that the odor remained unchanged, both from the point of view of its character and of its intensity.

EXAMPLE 4

Stability test in an antiperspirant composition for aerosol spray

An antiperspirant composition, intended to be applied by means of a spray type distributor, was prepared by admixing the following ingredients:

|  | Ingredients | % by weight |
|---|---|---|
| I. | Cyclomethicone[1] | 51.00 |
|  | Perfume[2] | 4.00 |
|  | Isopropyl myristate | 8.75 |
|  | Aerosil 200[3] | 1.00 |
|  | Bentone 38[4] | 3.25 |
|  | Aluminium chlorhydrate[5] | 32.00 |
|  | Total | 100.00 |

| Ingredients | % by weight |
|---|---|
| [1)]volatile silicone oil DC 344 and DC 345, in equal parts; origin: DOW Chemicals, USA | |
| [2)]see Example 1 | |
| [3)]origin: Degussa | |
| [4)]quaternium 18-hectorite; origin: NL Industries | |
| [5)]for example, Mico Dry Ultrafine; origin: Reheis Chem. Corp., USA | |

Part I was admixed and then Bentone 38 and Aerosil 200 were added thereto. The mixture was stirred for a few minutes with a high speed stirrer (for example, of the Ultra-Turray type, Homorex, Silverson) until a mixture as thick as possible was obtained. Finally, there was added the aluminum chlorhydrate under stirring. The whole was well mixed and then poured into aerosol containers, in a proportion of 25% of the mixture thus prepared to 75% of Drivosol 27 (propellant; origin:Hüls). The product thus obtained was tested under the conditions described in Example 3. According to the opinion of the panel of perfumers who evaluated the product after the one month test period, both the aspect and odor of the product remained perfectly unchanged.

EXAMPLE 5

Test of substantivity on linen

To an unperfumed commercial fabric softener base there was added, on the one hand, 0.1% of 5,6,7,8-tetrahydro-3,5,5,6,7,8,8-heptamethyl-2-naphthalenecarbonitrile and, on the other hand, 0.1% of 5,6,7,8-tetrahydro- 3,5,5,6,7,8,8-heptamethyl-2-naphthalenecarbaldehyde. Two standard batches of textiles were then treated with these two perfumed fabric softener samples in a washing cycle carried out in two separate washing machines, operating under the same conditions. The two batches of textiles were then evaluated on a blind test by a panel of 4 expert perfumers, just out of the machine, after drying and a week later. According to the opinion of the perfumers, the two batches of textiles developed the same odor, both when taken out of the machine and after drying. After a week, the textiles treated with the fabric softener containing 5,6,7,8-tetrahydro- 3,5,5,6,7,8,8-heptamethyl-2-naphthalenecarbonitrile were unanimously preferred by the perfumers, for the quality and strength of their musky odor, which remained practically unchanged in character and intensity since their treatment, whereas the odor of the other batch of textiles, while still quite perceptible, was already weaker.

EXAMPLE 6

Masculine cologne

A masculine cologne was prepared by admixing the following ingredients (parts by weight):

| Ingredients | Parts by weight |
|---|---|
| Linalyl acetate | 200 |
| Allylamyl glycolate | 80 |
| Bergamot | 500 |
| Linalol | 150 |
| Citral | 30 |
| 10% *α-Damascone[1)] | 70 |
| Dihydromyrcenol | 900 |
| Polysantol ® [1)3)] | 50 |
| 10% *Galbanum essential oil | 70 |
| Synthetic juniper oil | 60 |
| China geranium essential oil | 40 |
| 10% *Heliopropanal | 50 |
| Hedione ® [1)4)] | 230 |
| Iralia ® [1)5)] | 100 |
| Iso E Super[2)6)] | 130 |
| 10% *Labdanum Ciste | 50 |
| Lavandin essential oil | 150 |
| Lyral ® 2)7) | 100 |
| Brasilian mint essential oil | 15 |
| Methylnaphthylketone | 10 |
| Crystalmoss | 30 |
| Nutmeg essential oil | 50 |
| 1% *Methyl octynecarbonate | 35 |
| Portugal orange essential oil | 100 |
| Precyclemone ® B[2)8)] | 70 |
| Clary sage | 80 |
| Vertofix ® coeur[2)9)] | 300 |
| 10% *Zestover[1) 10)] | 70 |
| Galbex ® 183[1)] | 200 |
| Rose essential oil 193 D[1)] | 20 |
| Cetalox ® [1)11)] | 10 |
| Total | 3950 |

*in dipropyleneglycol
[1)]origin: Firmenich SA, Geneva, Switzerland
[2)]origin: IFF (International Flavors & Fragrances, USA)
[3)]3,3-dimethyl-5-(2',2',3'-trimethyl-3'-cyclopenten-1'-yl)-4-penten-2-ol
[4)]methyl 3-oxo-2-pentyl-cyclopentanacetate
[5)]methylionone
[6)]2,3,8,8,-tetramethyl-2-acetyl-1,2,3,4,5,6,7,8-octahydronaphthalene
[7)]4-(4-hydroxy-4-methylpentyl)-3-cyclohexene-1-carboxaldehyde
[8)]1-methyl-4-(4-methyl-3-pentenyl)-3-cyclohexene-1-carboxaldehyde
[9)]ketonic derivatives of Texas cedar essential oil
[10)]2,4-dimethyl-3-cyclohexene-1-carbaldehyde
[11)]dodecahydro-3a,6,6,9a-tetramethyl-naphtho[2.1b]furan When there were added to this composition 50 parts by weight of (−)-(6S,7S)- 5,6,7,8-tetrahydro-3,5,5,6,7,8,8-heptamethyl-2-naphthalenecarbaldehyde, a novel composition ("test") was obtained, the musky and amber character of which was distinctly more marked than that of the base composition. By comparing, on a blind test, with a novel composition containing an identical amount of the (+)-(6R, 7R) enantiomer, the test composition was found to be more powerful by a panel of eight perfumers.

What we claim is:

1. 5,6,7,8-Tetrahydro-3,5,5,6,7,8,8-heptamethyl-2-naphthalenecarbonitrile, as a racemate or in the form of one of its optically active isomers.

2. Trans-5,6,7,8-tetrahydro-3,5,5,6,7,8,8-heptamethyl-2-naphthalenecarbonitrile.

3. (−)-(6S,7S)-5,6,7,8-Tetrahydro-3,5,5,6,7,8,8-heptamethyl-2-naphthalenecarbonitrile.

4. (+)-(6R,7R)-5,6,7,8-Tetrahydro-3,5,5,6,7,8,8-heptamethyl-2-naphtalenecarbonitrile.

5. A method to confer, improve, enhance or modify the odor properties of a perfuming composition or a perfumed article, wherein there is added to said composition or article a fragrance effective amount of 5,6,7,8-tetrahydro- 3,5,5,6,7,8,8-heptamethyl-2-naphthalenecarbonitrile in racemic form, or in the form of one of its optically active isomers.

6. A perfuming composition or a perfumed article containing as an active ingredient 5,6,7,8-tetrahydro-3,5,5,6,7,8,8-heptamethyl-2-naphthalenecarbonitrile in racemic form or in the form of one of its optically active isomers.

7. A perfumed article according to claim 6, in the form of a perfume or a cologne, a soap, a bath or shower gel, a shampoo or other hair-care product, a cosmetic preparation an air or body deodorant, a detergent or fabric softener, or a household product.

8. The oxime of 5,6,7,8-tetrahydro-3,5,5,6,7,8,8-heptamethyl-2-naphthalenecarbaldehyde.

9. (−)-(6S,7S)-5,6,7,8-Tetrahydro-3,5,5,6,7,8,8-heptamethyl-2-naphthalenecarbaldehyde.

10. A method to confer, improve, enhance or modify the odor properties of a perfuming composition or a perfumed article, wherein there is added to said composition or article a fragrance effective amount of (−)-(6S,7S)- 5,6,7,8-tetrahydro-3,5,5,6,7,8,8-heptamethyl-2-naphthalenecarbaldehyde.

* * * * *